United States Patent [19]

Naitoh et al.

[11] Patent Number: 5,399,715

[45] Date of Patent: Mar. 21, 1995

[54] POLYAMINO OLIGOMERS AND POLYMALEIMIDE COMPOUNDS

[75] Inventors: Shigeki Naitoh, Tokyo; Yasuhiro Endo; Youichi Ueda, both of Tsukuba; Kunimasa Kamio, Toride, all of Japan

[73] Assignee: Sumitomo Chemical Company, Limited, Osaka, Japan

[21] Appl. No.: 66,099

[22] PCT Filed: Aug. 12, 1992

[86] PCT No.: PCT/JP92/01030

§ 371 Date: Jun. 2, 1993

§ 102(e) Date: Jun. 2, 1993

[87] PCT Pub. No.: WO93/12933

PCT Pub. Date: Jul. 8, 1993

[30] Foreign Application Priority Data

Dec. 27, 1991 [JP] Japan .................. 3-347108
Dec. 27, 1991 [JP] Japan .................. 3-347109
Mar. 6, 1992 [JP] Japan .................. 4-049360

[51] Int. Cl.$^6$ ............................ C07D 207/24
[52] U.S. Cl. ......................... 548/521; 548/520
[58] Field of Search .......................... 548/521

[56] References Cited

U.S. PATENT DOCUMENTS 3,365,347 1/1968 Lund et al. ................ 260/570
4,205,160 5/1980 Gloth et al. ................ 548/521

FOREIGN PATENT DOCUMENTS 2111194 9/1972 Germany .
61-44 1/1986 Japan .
62-155241 7/1987 Japan .
62-155242 7/1987 Japan .
63-35561 2/1988 Japan .................. 548/221
63-41456 2/1988 Japan .................. 548/221
8700835 2/1987 WIPO .................. 548/221

OTHER PUBLICATIONS

CA 107:23734; A new bismaleimide–chemistry and application. Lee et al., p. 2, 1987.
Chemitech, Aug. 1986, pp. 500–504, Howard A. Colvin et al., "Polymers from diisopropenyibenzene".

Primary Examiner—Mary C. Lee
Assistant Examiner—Joseph K. McKane
Attorney, Agent, or Firm—Stevens, Davis, Miller & Mosher

[57] ABSTRACT

The polyamino oligomers of this invention are obtained by reacting diisopropenylbenzenes or bis($\alpha$-hydroxyisopropyl)benzenes and anilines in the presence of an acid catalyst and characterized by the recurring unit having an indane skeleton. These polyamino oligomers can be used as curing agent for laminate resins. Also, they can be reacted with maleic anhydride to prepare polymaleimide compounds of this invention.

The polymaleimide compounds of this invention are low in melting point (or softening point) and, in combination with a substance producing three-dimensional crosslinkage such as triallyl isocyanurate, aromatic diamine, etc., can provide thermosetting resin compositions suited for producing copper-clad laminates. The copper-clad laminates obtained from the thermosetting resin compositions of this invention are low in dielectric constant, heat-resistant and also low in water absorptivity, so that they are useful for multi-layer printed boards.

1 Claim, No Drawings

POLYAMINO OLIGOMERS AND POLYMALEIMIDE COMPOUNDS

FIELD OF ART

This invention relates to novel polyamino oligomers, a process for preparing the same, polymaleimide compounds derived from said polyamino oligomers, resin compositions containing said compounds, and copper-clad laminates using said compositions.

The polyamino oligomers of this invention find a wide scope of use, such as preparation of curing agents for laminate resins which are low in melting point (or softening point) and desirably used without a solvent, and intermediates for various types of resins such as polymaleimide resins, polyamide resins, etc.

The polymaleimide compounds of this invention can be also used for laminate resins which are low in melting point, capable of use without a solvent and also low in dielectric constant and water absorptivity, and molding resins with excellent single workability.

BACKGROUND ART

As the art regarding the polyamino oligomers of this invention, there is known a process for preparing bis(p-aminocumyl)benzenes through acid catalytic reaction of aniline derivatives and diisopropenylbenzenes.

For instance, in German Patent No. 2,111,194, U.S. Pat. No. 3,365,347 and Japanese Patent Application Kokai No. 44/1986, it is proposed to react aniline derivatives and diisopropenylbenzenes under the appropriate conditions by using an acid catalyst and further carry out a purification operation such as crystallization for obtaining pure bis(p-aminocumyl)benzenes.

Bis(p-aminocumyl)benzenes obtained according to these methods are a crystalline solid with a melting point of 100° C. or higher, so that when they are blended in a resin, it is necessary to apply a pertinent treatment such as heating them to a temperature higher than their melting point or dissolving them in a suitable solvent. These treatments, however, would give rise to such problems as increase of viscosity of the resin due to the advancement of reaction and formation of voids in the course of curing reaction, so that a compound which unnecessitates these treatments has been desired.

The polymaleimide compounds are being made practical use of by utilizing their excellent heat resistance, but they have the defects that they singly are hard to dissolve in general-purpose organic solvents and are also low in water absorptivity and poor in electrical properties due to their high polarity.

For overcoming these defects, bis(p-aminocumyl)-benzenes obtained from an acid catalytic reaction of aniline derivatives and diisopropenylbenzenes, such as mentioned above, are further reacted with maleic anhydride in the presence of a dehydrating agent, a catalyst and a base to obtain bis(p-N-maleimidecumyl)benzenes, as described in International Application Laid-Open No. W087/00835. However, these compounds, being a crystalline solid with a high melting point, need to be subjected to a pertinent treatment such as melting by heating to a temperature above their melting point or dissolving in a suitable solvent, before molding. In the former case, since the difference between the compound melting point and the maleimide group reaction temperature is reduced, the time available for molding might be limited, and in the latter case, there is a risk of causing formation of voids in the course of molding.

Also, these compounds are not necessarily satisfactory in water resistance and electrical properties.

Thermosetting resins have been popularly used as matrix resin for printed wiring boards. With operational speedup of semiconductor elements in multi-layer printed wiring boards for high-speed computers in recent years, necessity is increasing for corresponding speedup of response of circuitries on the printed board. Signal propagation speed in circuitries on the printed board depends on dielectric constant of the insulating material holding the circuitries, and generally the lower the dielectric constant of a material, the higher signal propagation speed it offers. Hitherto, polyimide resins and heat resistant epoxy resins have been used for such purpose.

The conventional polyimide resins and heat resistant epoxy resins indeed have excellent heat resistance, but the dielectric constant of these resins as a single body is as high as 3.4 to 3.9, and the laminate made by combining such resin with E-glass cloth has even a higher order of dielectric constant, 4.5 to 5.0. For reducing dielectric constant of the laminates to less than 4.0, it was proposed to modify the resin with a pertinent substance such as polybutadiene, but this method involves the problem that heat resistance of resin is lowered, and for this reason, it has not been applied to practical use. Thus, a resin composition capable of forming a laminate with a dielectric constant of 4.0 or less without impairing heat resistance has been strongly desired.

In order to solve the above problem, it is necessary to prepare a resin composition using a polymaleimide compound derived from a polyamino compound into which a novel molecular structure having the effect of improving water resistance and electrical properties has been introduced, said resin compositions having a low melting point (softening point) and capable of use without a solvent for the improvement of moldability, and to apply such a resin composition as matrix resin for the laminates.

DISCLOSURE OF THE INVENTION

The present inventors have pursued strenuous studies for solving said problems and reached the present invention.

Thus, the present invention relates to novel polyamino oligomers, a process for preparing the same, polymaleimide compounds derived therefrom, resin compositions containing said compounds, and copper-clad laminates using said resin compositions.

First, the polyamino oligomers of this invention and a process for preparing such oligomers are described.

The polyamino oligomers are represented by the following formula (1):

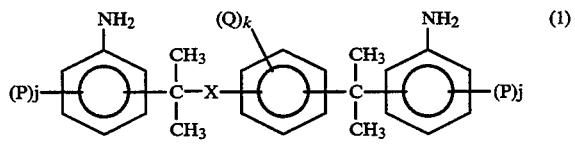

wherein P's represent independently an alkyl, alkyloxy or alkylthio group having 1 to 10 carbon atoms, an aryl, aryloxy or arylthio group having 6 to 10 carbon atoms, a cycloalkyl group having 5 to 10 carbon atoms, a halogen atom, a nitro group or a mercapto group; j represents an integer of 0 to 4; when j is 2 to 4, P's may be same or different in a same ring; Q's represent independently an alkyl, alkyloxy or alkylthio group having 1 to 10 carbon atoms, an aryl, aryloxy or arylthio group having 6 to 10 carbon atoms, a halogen atom, a hydroxyl group or a mercapto group; k represents an integer of 0 to 3; when k is 2 or 3, Q's may be same or different in a same ring; and X designates principally a structure represented by the formula (2):

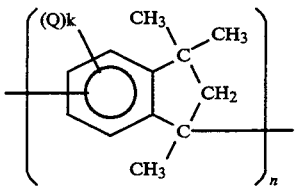
(2)

wherein Q and k are as defined above, and n is an average recurring unit number which is 0.5 to 20, and can be produced by reacting a compound represented by the formula (3):

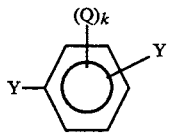
(3)

(wherein Y's represent independently a monovalent functional group selected from the group consisting of

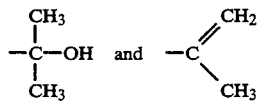

in which the ortho-position of at least one of 2 Y's is hydrogen atom; and Q and k are as defined above, and an aniline derivative represented by the formula (4):

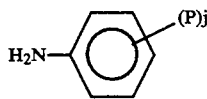
(4)

wherein at least one of the ortho- and para-positions of amino group is hydrogen atom; and P and j are as defined above, in the presence of an acid catalyst.

The polymaleimide compounds according to this invention are derived from said polyamino oligomers and represented by the formula (5):

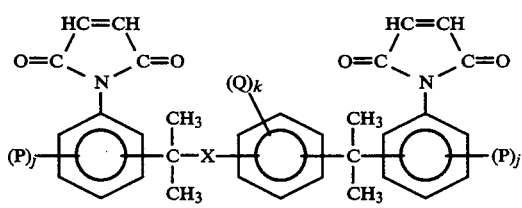
(5)

wherein P, Q, j, k and X represent the same as defined above in connection to the formula (1).

A thermosetting resin composition according to the present invention can be obtained by blending said polymaleimide compound (A) and a substance (B) which is reacted with said maleimide compound to produce three-dimensional crosslinkage. Further, a copper-clad laminate of this invention can be obtained by dissolving said thermosetting resin in an organic solvent, impregnating a substrate with the resulting solution, drying it, placing the resultantly obtained prepreg and a copper foil one on the other, and subjecting them to laminate molding under heating.

In the polyamino oligomers represented by the formula (1), X designates the structure of the above-shown formula (2), but when in the formula (4) representing aniline or its derivatives, j is 3 or less and at least 2 of the ortho- and para-positions of amino group are hydrogen atoms, the structure represented by the formula (6):

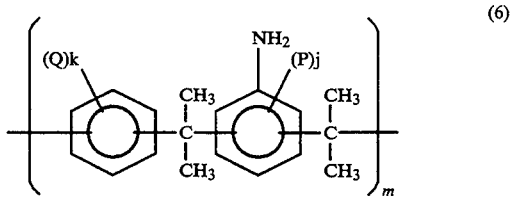
(6)

wherein P, Q, j and k are as defined above, and m is a recurring unit number which is an integer of 1 to 20, may be included in the concept of the structure designated by X.

In the structure of the formula (2) featuring the polyamino oligomers and polymaleimide compounds according to the present invention, the recurring unit number n should be in the range of 0.5 to 20, preferably 0.5 to 10, as mean value, for providing said substances which are low in melting point (softening point), also low in melt viscosity and excellent in workability. When n is less than 0.5, the content of the high-melting material becomes too large, while whenn exceeds 20, the functional group density is lowered, resulting in reduced heat resistance of the composition.

The compound of the formula (3) (hereinafter referred to as compound (C)) used in the present invention is not specifically defined, but typically there can be used p- and m-diisopropenylbenzenes, p- and m-bis-(α-hydroxyisopropyl)benzene, 1-(α-hydroxyisopropyl)-3-isopropenylbenzene, and mixtures thereof. It is also possible to use nuclear alkyl group substituents of these compounds, such as diisopropenyltoluene and bis(α-hydroxyisopropyl)toluene, and nuclear halogen substituents such as chlorodiisopropenylbenzene and chlorobis(α-hydroxyisopropyl)benzene.

Other examples of the compounds (C) usable in this invention include: 2-chloro-1,4-diisopropenylbenzene, 2-chloro-1,4-bis(α-hydroxyisopropyl)benzene, 2-bromo-1,4-diisopropenylbenzene, 2-bromo-1,4-bis(α-hydroxyisopropyl)benzene, 2-bromo-1,3-diisopropenylbenzene, 2-bromo-1,3-bis(α-hydroxyisopropyl)benzene, 4-bromo-1,3-diisopropylbenzene, 4-bromo-1,3-bis(α-hydroxyisopropyl)benzene, 5-bromo-1,3-diisopropenylbenzene, 5-bromo-1,3-bis(α-hydroxyisopropyl)benzene, 2-methoxy-1,4-diisopropenylbenzene, 2-methoxy-1,4-bis(α-hydroxyisopropyl)benzene, 5-ethoxy-1,3-diisopropenylbenzene, 5-ethoxy-1,3-bis(α-hydroxyisopropyl)benzene, 2-phenoxy-1,4-diisopropenylbenzene, 2-phenoxy-1,4-bis(α-hydroxyisopropyl)benzene, 2-methylthio-1,4-diisopropenylbenzene, 2-methylthio-1,4-bis(α-hydroxyisopropyl)benzene, 2-phenylthio-1,3-diisopropenylbenzene, 2-phenylthio-1,3-bis(α-hydroxyisopropyl)benzene, 2-phenyl-1,4-diisopropenylbenzene, 2-phenyl-1,4-bis(α-hydroxyisopropyl)benzene, 5-naphthyl-1,3-diisopropenylbenzene, 5-napthyl-1,3-bis-(α-hydroxyisopropyl)benzene, 2-methyl-1,4-diisopropenylbenzene, 2-methyl-1,4-bis(α-hydroxyisopropyl)benzene, 5-butyl-1,3-diisopropenylbenzene, and 5-butyl-1,3-bis(α-hydroxyisopropyl)benzene.

As the compound of the formula (4) (hereinafter referred to as compound (D)), there can typically be used aniline and its derivatives such as chloroaniline, dichloroaniline, toluidine, xylidine, phenylaniline, nitroaniline, aminophenol and cyclohexylaniline.

Other examples of the compounds (D) usable in this invention include methoxyaniline, ethoxyaniline, phenoxyaniline, naphthoxyaniline, aminothiol, methylthioaniline, ethylthioaniline and phenylthioaniline.

In the process for preparing the polyamino oligomers represented by the formula (1) and having the structure characteristic of the present invention, compound (C) and compound (D) are reacted by initially feeding them in a compound (D) to compound (C) molar ratio of 0.1–2.0, preferably 0.2–1.0, and then further supplying compound (D) in an amount corresponding to (D) to (C) ratio of 0.5–20.0, preferably 1.0–5.0. This two-stage reaction is favorable in view of perfection of reaction and facilitation of operation.

The acid catalysts usable for the above reaction include inorganic acids such as hydrochloric acid and sulfuric acid, organic acids such as benzenesulfonic acid and toluenesulfonic acid, solid acids such as activated clay, acidic clay, silicaalumina, zeolite and strongly acidic ion exchange resins, heteropoly-hydrochloric acid, and the like. Among them, the solid acids which can be easily cleared of catalyst by filtration after reaction are preferred because of simple operation. In case of using other acids, it would be necessary to perform neutralization with a base after reaction and washing with water.

The amount of said acid catalyst used in the reaction is in the range of 5 to 40% by weight based on the total amount of the initially charged compounds (C) and (D), but for the operational and economical reasons, it is preferably in the range of 10 to 30% by weight.

Reaction temperature is usually selected from the range of 100° to 300° C., but it is preferably in the range of 160° to 230° C. for suppressing generation of isomers and avoiding side reactions such as thermal decomposition.

As for the reaction time, in view of the fact that the reaction may fail to advance to perfection in a short time while when a long time is used for the reaction, there may collaterally occur side reactions such as thermal decomposition reaction of the product, reaction time is usually selected from the range of 2 to 48 hours, preferably 6 to 24 hours, in total reaction hours, assuming that the reaction is carried out under said temperature condition.

In the preparation of polyamino oligomers according to the present invention, aniline or a derivative thereof serves as a solvent, so that no other solvent needs to be used, but in certain cases, a solvent may be used. For instance, in the case of a reaction system which involves a dehydration reaction, more specifically in case of carrying out a reaction by using a compound having α-hydroxypropyl group as starting material, a process may be employed in which the primary reaction is conducted in said temperature range after completing the dehydration reaction by using a solvent capable of azeotropic dehydration, such as toluene or chlorobenzene, and distilling away the solvent.

The polymaleimide compound used in the present invention has a skeleton of the formula (5) as described above. In the formula (5), X designates a structure represented by the formula (2), but when j in the formula (2) representing aniline and its derivatives is 3 or less and at least 2 of the ortho- and para-positions of amino group are hydrogen atom, the structure corresponding to the formula (6), that is, the structure represented by the formula (7) is also embraced within the concept of the structure of X.

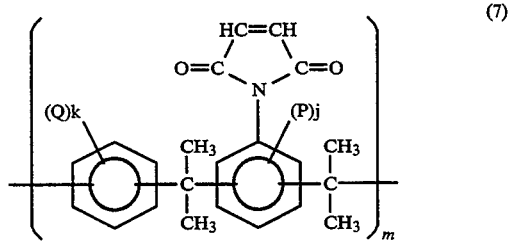

wherein P, Q, j, k and m represent the same as defined above. The average recurring unit number n is preferably 0.5 to 10 in view of low softening point, low melt viscosity, high heat deformation temperature and high glass transition point.

A polymaleimide compound of this invention can be obtained from a process which comprises feeding a polyamino oligomer of the formula (5), obtained in the manner described above, into a reactor, dissolving said oligomer in a proper solvent, reacting the oligomer with maleic anhydride in the presence of a dehydrating agent, a catalyst and a base, removing after the reaction unreacted maleic anhydride and other impurities by washing with water or other means, and further removing the solvent under reduced pressure.

The organic solvents usable in the above reaction include ketones such as acetone, methyl ethyl ketone, methyl isobutyl ketone, cyclohexanone and acetophenone, aprotic solvents such as N,N-dimethylformamide, N,N-dimethylacetamide, dimethyl sulfoxide, N-methyl-2-pyrrolidone, acetonitrile and sulforan, cyclic ethers such as dioxane and tetrahydrofuran, esters such as ethyl acetate and butyl acetate, and halogen type solvents such as chlorobenzene, dichlorobenzene, chloroform, carbon tetrachloride, dichloroethane and trichloroethane. Of these solvents, methyl isobutyl ketone is especially preferred.

In the above polymaleimide forming reaction, a good result is obtained when a polyamino oligomer and maleic anhydride are supplied in a ratio of maleic anhydride to amino equivalent of polyamino oligomer of 1–1.5, preferably 1.1–1.2, and they are reacted in an organic solvent of the amount of 1 to 50 by weight ratio, preferably 2 to 5 by weight ratio based on the total amount of said polyamino oligomer and maleic anhydride.

As the dehydrating agent in the above reaction, there can be used lower aliphatic carboxylic acid anhydrides such as acetic anhydride, propionic anhydride and butyric anhydride, oxides such as phosphorus pentoxide, calcium oxide and barium oxide, inorganic acids such as sulfuric acid, and porous ceramics such as molecular sieves. Acetic anhydride is preferred.

The catalysts usable in the above reaction include inorganic salts such as acetates, chlorides, bromides, sulfates and nitrates of nickel, cobalt, sodium, calcium, iron, lithium, manganese, etc. Nickel acetate is especially preferred.

The bases usable in the above reaction include tertiary amines such as triethylamine, tri-n-butylamine, N-methylpiperazine, N,N-dimethylbenzylamine and 1,8-diazabicyclo[5.4.0]-7-undecene, and inorganic alkalis such as carbonates of sodium and potassium. Triethylamine is preferred.

The amounts of the dehydrating agent, catalyst and base used in the above polymaleimide forming reaction are not critical, but usually dehydrating agent is used in an amount of 1 to 3 moles, preferably 1 to 1.5 moles, catalyst in an amount of 0.0001 to 1.0 mole, preferably 0.001 to 0.1 mole, and base in an amount of 0.01 to 1.0 mole, preferably 0.05 to 0.5 moles, to one equivalent of amino group of polyamine.

As for the polymaleimide forming reaction conditions, a polyamino oligomer and maleic anhydride are supplied in the above-specified ratio and reacted at a temperature of 10° to 100° C., preferably 30° to 50° C., for one to 12 hours, preferably 4 to 8 hours, after which a dehydrating agent, a catalyst and a base, such as mentioned above, are added and the mixture is further reacted at 20° to 110° C., preferably 50° to 80° C., for 2 to 24 hours, preferably 6 to 10 hours.

The thermosetting resin compositions according to the present invention comprise a polymaleimide compound (A) of the formula (1) and a substance (B) reacted therewith.

As said reaction substance (B), a material which generates three-dimensional crosslinkage on reaction with the unsaturated bonds of the polymaleimide compound is used. Preferred examples of such substance (B) are triallyl isocyanurate and aromatic diamines.

The following can be cited as examples of said aromatic diamines: 4,4'-diaminodiphenylmethane, 3,3'-diaminodiphenylmethane, 4,4'-diaminodiphenyl ether, 3,4'-diaminodiphenyl ether, 2,2-bis(4-aminophenoxy)propane, 2,2-bis(4-aminophenoxy)hexafluoropropane, 4,4'-diaminodiphenylsulfone, 3,3'-diaminodiphenylsulfone, 4,4'-diaminobenzophenone, 3,3'-diaminobenzophenone,3,3'-diaminobenzophenone, 2,4-toluenediamine, 2,6-toluenediamine, m-phenylenediamine, p-phenylenediamine, benzidine, 4,4'-diaminodiphenyl sulfide, 3,3'-dichloro-4,4'-diaminodiphenylsulfone, 3,3'-dichloro-4,4'-diaminodiphenylpropane, 3,3'-dimethyl-4,4'-diaminodiphenylmethane, 3,3-dimethoxy-4,4'-diaminobiphenyl, 3,3'-dimethyl-4,4'-diaminobiphenyl, 1,3-bis(4-aminophenoxy)benzene, 1,3-bis(3-aminophenoxy)benzene, 1,4-bis(4-aminophenoxy)benzene, 2,2-bis(4-aminophenoxyphenyl)propane, 2,2-bis(4-aminophenoxyphenyl)hexafluoropropane, 4,4'-bis(4-aminophenoxy)diphenylsulfone, 4,4'-bis(3-aminophenoxy)diphenylsulfone, 9,9'-bis(4-aminophenyl)fluorene, 3,3'-dicarboxy-4,4'-diaminodiphenylmethane, 2,4-diaminoanisole, bis(3-aminophenyl)methylphosphine oxide, 4,4'-methylene-bis-o-chloroaniline, tetrachlorodiaminodiphenylmethane, m-xylenediamine, p-xylenediamine, 4,4'-diaminostilbene, 5-amino-1-(4'-aminophenyl)-1,3,3-trimethylindane, 6-amino-1-(4'-aminophenyl)-1,3,3-trimethylindane, 5-amino-6-methyl-1-(3'-amino-4'-methylphenyl)-1,3,3-trimethylindane, 7-amino-6-methyl-1-(3'-amino-4'-methylphenyl)-1,3,3-trimethylindane, 6-amino-5-methyl-1-(4'-amino-3'-methylphenyl)-1,3,3-trimethylindane, and 6-amino-7-methyl-1-(4'-amino-3'-methylphenyl)-1,3,3-trimethylindane. These compounds may be used either singly or in combination.

The polyamino oligomers of this invention may also be used as reaction substance (B).

The resin compositions of this invention may contain other types of compound, for example, a compound having alkenyl group such as bismaleimide, allyl ether type compound, triallyl cyanurate, alkenylphenol type compound, compound having vinyl group or the like within limits not affecting the object of the invention. It is also possible to blend other thermosetting resins such as thermosetting polyimide resin, epoxy resins, phenol resin, cyanate resin and the like according to the purpose of use of the product.

Typically, a flame retardant having a reactive group may be added for the purpose of affording flame retardancy to the laminate, such agent is preferably blended in such an amount that the ratio of bromine in the resin will be in the range of 5 to 20% by weight.

The quantitative proportions of the compounds of the resin compositions according to this invention can be properly selected according to the desired performance of the product, but in the case of triallyl isocyanurate, it is preferably blended in such an amount that its ratio to the whole composition will be 5 to 50% by weight, more preferably 10 to 30% by weight. In the case of aromatic diamine, it is preferably blended such that the molar ratio of double bonds of polymaleimide compound to active hydrogen of aromatic diamine (double bond/active hydrogen molar ratio) will be 0.5–2.0, more preferably 0.8–1.5.

The heat curing reaction for the resin compositions of this invention can be easily accomplished without a catalyst, but for performing the reaction quickly, it is effective to add a polymerization initiator such as an organic peroxide or azo compound and/or a basic catalyst such as a phosphine type compound or a tertiary amine. Typical examples of such agents are benzoyl peroxide, dicumyl peroxide, azobisisobutyronitrile, triphenylphosphine, triethylamine and imidazoles. The amount of such an agent added is preferably 0.05 to 5% by weight based on the whole resin composition.

A copper-clad laminate using a thermosetting resin composition of this invention can be produced according to the conventional method. That is, a resin varnish is prepared by dissolving said resin composition in an organic solvent, then a substrate is impregnated with said resin varnish and heat treated to form a prepreg, and this prepreg and a copper foil are subjected to laminate molding under heating to obtain a copper-clad laminate.

The organic solvent used in the above process can be properly selected from various types of solvent such as toluene, xylene, N,N-dimethylformamide, N,N-dimethylacetamide, N-methyl-2-pyrrolidone, methyl ethyl ketone, methyl isobutyl ketone, dioxane, tetrahydrofuran and the like, which may be used either singly or in combination.

The substrate to be impregnated with said resin varnish may be a woven or non-woven fabric, mat, paper or the like, made of inorganic or organic fibers such as glass fiber, polyester fiber, polyamide fiber, etc., and these may be used either singly or in combination.

The heat treating conditions for the prepreg are properly selected according to the type and amount of solvent, catalyst and various other additives added, but usually said heat treatment is carried out at a temperature of 80° to 220° C. for a period of 3 to 30 minutes.

Heat molding in this invention can be accomplished by, for example, hot press molding conducted at a temperature of 150°–300° C. under a pressure of 10–100 kg/cm² for a period of 20–300 minutes.

BEST MODE FOR CARRYING OUT THE INVENTION

EXAMPLES

The present invention will be described more particularly below with reference to the examples thereof, which examples, however, are merely intended to be illustrative and not to be construed as limiting the scope of the invention in any way.

Example 1

Preparation of 2,6-xylidine oligomer 972 g (6.15 mol) of m-di($\alpha$-hydroxyisopropyl)benzene, 303 g (2.50 mol) of 2,6-xylidine, 1,275 g of xylene and 334 g of acid clay were supplied into a 5,000 ml reactor equipped with a reflux condenser adapted with a Dean Stark apparatus for water separation, a thermometer, a stirrer and a nitrogen introducing means, and the mixture was heated with stirring until the internal temperature reached 120° C. Then the mixture was further heated while removing the aqueous distillate by the Dean Stark apparatus until the internal temperature reached 210° C. and was maintained at this temperature for 3 hours.

The total amount of aqueous distillate at this point was 214.4 g. Then the mixture was cooled to an internal temperature of 140° C., after which 1,052 g (8.69 mol) of 2,6-xylidine was fed and the mixture was heated to an internal temperature of 220° C. and maintained at this temperature for 3 hours. After completion of the reaction, the mixture was cooled to an internal temperature of 100° C. or below, diluted with 1,500 g of toluene and filtered to remove acid clay. Then the solvent and low-molecular weight matter such as unreacted substances were distilled away under reduced pressure to obtain 1,310 g of the objective 2,6-xylidine oligomer. The amine equivalent of this product was 292 g/eq and its softening point was 60.6° C.

Infrared absorption spectrum of the product showed absorption at 2960 cm$^{-1}$, 1490 cm$^{-1}$, 1461 cm$^{-1}$, 1440 cm$^{-1}$ and 755 cm$^{-1}$, which is typical of the indane skeleton of the formula (2).

FD-MS spectrometry of the product detected m/e=400 (n'=0), 558 (n'=1), 716 (n'=2) and 874 (n'=3) as main peaks corresponding to the formula (1) where X designates the structure of the formula (2).

In the above and following descriptions of FD-MS spectrometry, n' denotes the recurring unit number of X. The average recurring unit number n (number average) of the formula (2), as determined by liquid chromatography using the calibration curves based on the results of mass spectrometric analysis, was 0.92.

Example 2

Preparation of o-toluidine oligomer 271 g (1.4 mol) of m-bis($\alpha$-hydroxyisopropyl)benzene, 37.5 g (0.35 mol) of o-toluidine, 308.5 g of xylene and 65.3 g of acid clay were fed into a 2,000 ml reactor equipped with a reflux condenser adapted with a Dean Stark apparatus for water separation, a thermometer, a stirrer and a nitrogen introducing means, and the mixture was heated with stirring until the internal temperature reached 120° C. Then the mixture was further heated to an internal temperature of 210° C. while removing the aqueous distillate by the Dean Stark apparatus and maintained at this temperature for 7 hours.

The total amount of the aqueous distillate at this point was 57.0 g. Then the mixture was cooled to an internal temperature of 140° C. added with 7 5 g (0.7 mol) of o-toluidine, again heated to an internal temperature of 210° C. and maintained at this temperature for 12 hours. The resulting reaction mixture was cooled until the internal temperature became 100° C. or below, and diluted with 313.1 g of toluene. Then acid clay was removed by filtration and the solvent and low-molecular weight matter such as unreacted substances were distilled away under reduced pressure to obtain 254.8 g of the objective o-toluidine oligomer. The amine equivalent of this product was 393 g/eq and its softening point was 64.8° C. The average recurring unit number n (number average) in the formula (2), as determined by liquid chromatography, was 2.6.

Example 3

Preparation of aniline oligomer 158 g (1.0 mol) of 1,3-diisopropenylbenzene, 46.5 g (0.5 mol) of aniline and 20 g of acid clay were supplied into a 500 ml reactor provided with a reflux condenser, a thermometer, a stirrer and a nitrogen introducing means, and the mixture was heated with stirring until the internal temperature reached 220° C. and maintained at this temperature for 3 hours. Then the mixture was cooled to an internal temperature of of 150° C. or below, added with 232.5 g (2.5 mol) of aniline, again heated to an internal temperature of 175° C. and maintained at this temperature for 3 hours. After completion of the reaction, the mixture was cooled to 140° C. or below, then acid clay was removed by filtration and the low-molecular weight matter such as unreacted substances were distilled away under reduced pressure to obtain. 190.2 g of the objective aniline oligomer. The amine equivalent of this product was 225 g/eq and its softening point was 54.7° C.

Infrared absorption spectrum of the obtained product showed absorption at 2964 cm$^{-1}$, 1487 cm$^{-1}$, 1465 cm$^{-1}$, 1414 cm$^{-1}$ and 754 cm$^{-1}$, which is typical of the indane skeleton.

FD-MS spectrometry of the product detected m/e=344 (n'=0), 502 (n'=1), 660 (n'=2) and 818 (n'=3) as peaks corresponding to the formula (1) where X designates the structure of the formula (2) alone, and m/e=595 (n'=1), 753 (m=1, n'=1), 911 (m=2, n'=1), 1004 (m=1, n'=2), 1069 (m=3, n'=1), 1162 (m=2, n'=2), 1256 (m=1, n'=3), 1321 (m=3, n'=2) and 1414 (m=2, n'=3) as peaks corresponding to the formula (1) where X includes the structure of the formula (5) beside the structure of the formula (2).

The average recurring unit number n in the formula (2) as determined by liquid chromatography was 1.85.

Example 4

Synthesis of 2,6-xylidine oligomer polymaleimide compound

A preparation process for a polymaleimide compound used in this invention comprising a reaction of 2,6-xylidine oligomer and maleic anhydride is described here.

308 g (1.05 equivalent, amino group equivalent: 292 g/eq) of 2,6-xylidine oligomer obtained in Example 1, 113.8 g (1.16 mol) of maleic anhydride and 984.2 g of methyl isobutyl ketone were supplied into a 5,000 ml reactor equipped with a reflux condenser, a thermometer, a stirrer and a nitrogen introducing means. The materials were dissolved with stirring at room temperature, and the resulting mixture was heated to 40° C. and maintained at this temperature for 6 hours. Then 151.8 g (1.05 mol) of acetic anhydride, 1.10 g (3.78 mmol) of nickel acetate tetrahydrate and 7.94 g (78.6 mmol) of triethylamine were added and the mixture was heated to 60° C. and maintained at this temperature for 8 hours. After the reaction, the mixture was cooled to room temperature, diluted with 703 g of methyl isobutyl ketone and washed with a dilute aqueous solution of sodium hydrogencarbonate and then with water, followed by azeotropic dehydration. Then the inorganic salts were filtered out and the solvent was removed under reduced pressure to obtain 305.8 g of the objective polymaleimide compound. The softening point of the obtained compound was 98.1° C.

Infrared absorption spectrum of the product showed absorption (at 2960 $cm^{-1}$, 1485 $cm^{-1}$, 1460 $cm^{-1}$, 1440 $cm^{-1}$ and 760 $cm^{-1}$) attributable to indane structure and absorption (at 1715 $cm^{-1}$ and 1805 $cm^{-1}$) attributable to maleimide structure.

Example 5

Synthesis of o-toluidine oligomer polymaleimide compound

A preparation process for a polymaleimide compound used in this invention comprising a reaction of o-toluidine oligomer and maleic anhydride is described here.

100 g (0.254 equivalent, amino group equivalent: 393 g/eq) of o-toluidine oligomer obtained in Example 2, 29.9 g (0.305 mol) of maleic anhydride and 303.3 g of acetone were supplied into a 2,000 ml reactor equipped with a reflux condenser, a thermometer, a stirrer and a nitrogen introducing means. The materials were dissolved with stirring at room temperature, and the resulting mixture was heated to 40° C. and maintained at this temperature for 9 hours. Then 33.8 g (0.331 mol) of acetic anhydride, 0.28 g (1.1 mol) of nickel acetate tetrahydrate and 1.92 g (19.0 mol) of triethylamine were added and the mixture was heated to 60° C. and maintained at this temperature for 8 hours. After the reaction, the mixture was cooled to room temperature, diluted with 303.0 g of toluene and washed with a dilute aqueous solution of sodium hydrogencarbonate and then with water, followed by azeotropic dehydration. Then the inorganic salts were filtered out and the solvent was removed under reduced pressure to obtain 101.9 g of the objective polymaleimide compound. This compound had a softening point of 110° C.

Infrared absorption spectrum of the product showed absorption (at 2960 $cm^{-1}$, 1490 $cm^{-1}$, 1460 $cm^{-1}$, 1430 $cm^{-1}$ and 765 $cm^{-1}$) attributable to indane structure and absorption (at 1715 $cm^{-1}$ and 1805 $cm^{-1}$) attributable to maleimide structure.

Example 6

Production of cured products and evaluation thereof

A process for producing a cured product by copolymerization of the 2,6-xylidine oligomer polymaleimide compound obtained in Example 4 and an aromatic diamine, and evaluation of properties of the obtained cured product are described.

372 g of 2,6-xylidine oligomer polymaleimide compound and 39.6 g of 4,4'-diaminodiphenylmethane were melted and mixed together by heating without using a solvent, and the mixture was press molded under 500 kg/$cm^2$ at 200° C. for one hour and then further heated at 200° C. for 4 hours and at 250° C. for 5 hours to obtain a cured molding having a thickness of 2 mm. Heat resistance, electrical properties and water resistance of the thus obtained cured molding were evaluated. The results are shown in Table 1.

Comparative Example 1

A process for producing a cured product by copolymerization of N,N-(4,4'-diaminodiphenylmethane)bismaleimide and an aromatic diamine, and the properties of the obtained cured product are described here.

179 g of N,N-(4,4'-diaminodiphenylmethane)bismaleimide and 39.6 g of 4,4'-diaminodiphenylmethane were melted and mixed together by heating without using a solvent, and the mixture was press molded under 50 kg/$cm^2$ at 200° C. for one hour and then heated at 200° C. for 4 hours to obtain a cured molding having a thickness of 2 mm. The properties of the obtained cured molding are shown in Table 1.

TABLE 1

| Items | | Examples | |
|---|---|---|---|
| | | Example 1 | Comp. Example |
| Resin components | PMI (g)*1 | 372.0 | — |
| | BMI (g)*2 | — | 179.0 |
| | DDM (g)*3 | 39.6 | 39.6 |
| Properties of cured products | Glass transition temperature (TMA. °C.) | 180 | 189 |
| | Coefficient of thermal expansion ((1/°C.) × $10^5$) | 5.5 | 5.8 |
| | Dielectric constant (—) | 2.95 | 3.20 |
| | Boiling water absorptivity (%) | 0.58 | 2.50 |

*1 2,6-xylidine oligomer polymaleimide compound obtained in Example 1
*2 N,N'-(4,4'-diaminodiphenylmethane)bismaleimide
*3 4,4'-diaminodiphenylmethane Property evaluations were made according to the following methods.

Glass transition temperature and coefficient of thermal expansion

Measured by using a thermal analyzer DT-30 and a thermal mechanical analyzer TMA-30M mfd. by Shimadzu Corp.

Dielectric constant

Electrodes were formed by metal coating on both sides of the cured product having a thickness of about 2 mm and the electrostatic capacity thereof was determined by using a multi-frequency LCR meter 4275A mfd. by Yokogawa Hewlett-Packard Co., and dielectric constant was calculated from the determined value of electrostatic capacity. The measurement was effected at 1 MHz.

Boiling water absorptivity

Calculated from the change in weight of the product after left in boiling water for 24 hours.

Examples 7–11

The polymaleimide compound obtained in Example 4 and various aromatic diamine compounds were blended in the ratios shown in Table 2, and they were melted and mixed together by heating without using a solvent to obtain the homogeneous resin mixtures. These resin mixtures were press molded at 200° C. for 2 hours and then postcured at 250° C. for 5 hours to obtain the cured resin products. Glass transition temperature and dielectric constant of these cured resin products were determined. Glass transition temperature was determined by the thermal analyzer DT-30 (Shimadzu Corp.) and dielectric constant was calculated from the electrostatic capacity of the sample at room temperature and 1 MHz determined by the multi-frequency LCR meter 4275A (Yokogawa Hewlett-Packard Co.). The results are shown in Table 2.

Comparative Example 2

A blend of N,N'-(4,4'-diaminodiphenylmethane)bis-maleimide (Bestlex BH-180 produced by Sumitomo Chemical Co., Ltd.) and 4,4'-diaminodiphenylmethane (Sumicure M produced by Sumitomo Chemical Co., Ltd.) were melted and mixed together by heating without using a solvent, and the mixture was subjected to the same treatments as in Examples 7–11 except that postcuring was conducted at 200° C. for 3 hours to obtain a cured resin product. Glass transition temperature and dielectric constant of this product were determined in the same way as in Examples 7–11. The results are shown in Table 2.

Glass transition temperature, copper foil peel strength, soldering heat resistance, boiling water absorptivity and dielectric constant of the obtained laminates were determined. Glass transition temperature was determined by using a dynamic visco-elastometer rheolographsolid mfd. by Toyo Seiki K.K., based on the temperature at which loss elastic modulus is maximized. Dielectric constant was calculated from the electrostatic capacity of the sample at room temperature and 1 MHz determined by the multi-frequency LCR meter 4275A (Yokogawa Hewlett-Packard). Other laminate properties were determined according to JIS-C-6481. The results of determinations are shown in Table 3.

Example 14

The polymaleimide compound obtained in Example 4 and 4,4'-diaminodiphenylmethane (Sumicure M produced by Sumitomo Chemical Co., Ltd) were dissolved in toluene to obtain a resin varnish, and by using this varnish, a copper-clad laminate was made in the same

TABLE 2

| Items | | Examples | | | | | |
|---|---|---|---|---|---|---|---|
| | | Example 7 | Example 8 | Example 9 | Example 10 | Example 11 | Comp. Example 12 |
| Resin formulation | Polymaleimide compound of Example 4 (g) | 447.0 | 447.0 | 447.0 | 447.0 | 447.0 | — |
| | 4,4'-diaminodiphenyl-methane (g) | 39.6 | — | — | — | — | 39.6 |
| | 2,2-bis(4-aminophenoxy-phenyl)propane | — | 82.0 | — | — | — | — |
| | 1,3-bis(3-aminophenoxy)-benzene (g) | — | — | 58.4 | — | — | — |
| | 1,4-bis(4-aminophenoxy)-benzene (g) | — | — | — | 58.4 | — | — |
| | 2,2-bis(4-aminophenyl)-hexafluoropropane | — | — | — | — | 66.8 | — |
| | N,N-(4,4'-diaminodiphenyl-methane)bismaleimide | — | — | — | — | — | 179.0 |
| Properties | Glass transition temperature (°C.) | 180 | 180 | 175 | 187 | 210 | 189 |
| | Dielectric constant (1 MHz) | 3.0 | 2.9 | 3.0 | 3.0 | 3.0 | 3.5 |

Examples 12 and 13

The polymaleimide compounds obtained in Examples 4 and 5 and triallyl isocyanurate were dissolved in toluene to obtain homogeneous resin varnishes. A glass cloth (E-glass KS-1600 produced by Kanebo, Ltd.) was impregnated with each of these resin varnishes and heat treated in an 80° C. hot-air dryer for 10–20 minutes to form a prepreg. 6 sheets of this prepreg and a copper foil (TTAI treated copper foil produced by Furukawa Denko K.K., 35 μm thick) were placed one on the other and press molded under a pressure of 50 kg/cm² at 200° C. for 2 hours, followed by curing at 250° C. for 5 hours to obtain a 1 mm thick copper-clad laminate.

way as Example 12. The properties of the obtained copper-clad laminate were determined by the same methods as used in Example 12. The results are shown in Table 3.

Comparative Example 3

N,N'-(4,4'-diaminodiphenylmethane)bismaleimide (Bestlex BH-180) and 4,4'-diaminodiphenylmethane (Sumicure M) were dissolved in N,N-dimethylformamide to prepare a resin varnish, and by using this resin varnish, a copper-clad laminate was made in the same way as Examples 12–13 except that postcuring was conducted at 200° C. for 3 hours. The properties of the obtained laminate were determined by the same methods as used in Example 12. The results are shown in Table 3.

TABLE 3

| Items | | Examples | | | Comp. Example 3 |
|---|---|---|---|---|---|
| | | Example 2 | Example 3 | Example 4 | |
| Resin formulation | Polymaleimide compound of Example 4 (g) | 376.0 | — | — | — |
| | Polymaleimide compound of Example 4 (g) | — | 447.0 | 447.0 | — |
| | Triallyl isocyanurate (g) | 83.1 | 83.1 | — | — |
| | 4,4'-diaminodiphenylmethane (g) | — | — | 39.6 | 39.6 |
| | N,N'-(4,4'-diaminodiphenyl-methane)-bismaleimide | — | — | — | 179.0 |
| Laminate properties | Glass transition temperature (°C.) | 226 | 247 | 229 | 235 |
| | Copper foil peel strength (kg/cm) | 1.4 | 1.4 | 1.5 | 1.4 |

TABLE 3-continued

| Items | Example 2 | Example 3 | Example 4 | Comp. Example 3 |
|---|---|---|---|---|
| Dielectric constant (1 MHz) | 3.8 | 3.9 | 4.0 | 4.6 |
| Soldering heat resistance (260° C., 3 min., normal state) | No abnormality | No abnormality | No abnormality | No abnormality |
| Soldering heat resistance (260° C., 3 min., after 2-hour boiling) | No abnormality | No abnormality | No abnormality | No abnormality |
| Boiling water absorptivity (24 hr) | 0.16 | 0.67 | 0.58 | 0.97 |

Industrial Applicability

The polyamino oligomers of this invention can be used as curing agent for laminate resins which are low in melting point (or softening point) and desirably used without a solvent. They are also useful as base material or intermediates of various types of resin.

The polymaleimide compounds of this invention, because of low melting point (or low softening point), are capable of use without a solvent and also excellent in workability in forming cured moldings. The obtained moldings are low in dielectric constant and also low in water absorptivity, so that they can be advantageously used as laminate resins or molding resins with excellent single workability.

The thermosetting resin compositions of this invention and the copper-clad laminates obtained therefrom have excellent heat and water resistance and low dielectric constant, so that they find particularly useful application to multi-layer printed boards.

We claim:

1. Polymaleimide compounds represented by the formula (5):

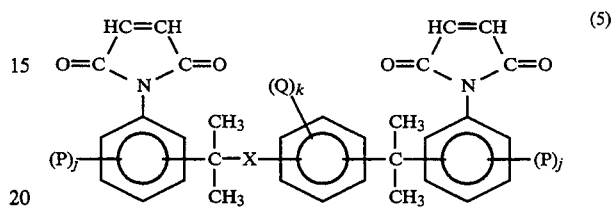

wherein P represents independently an alkyl, alkyloxy or alkylthio group having 1 to 10 carbon atoms, an aryl, aryloxy or arylthio group having 6 to 10 carbon atoms, a cycloalkyl group having 5 to 10 carbon atoms, a halogen atom, a nitro group, a hydroxyl group or a mercapto group; j represents an integer of 0 to 4; when j is 2 to 4, P may be same or different in a same ring; Q represents independently an alkyl, alkyloxy or alkylthio group having 1 to 10 carbon atoms, an aryl, aryloxy or arylthio group having 6 to 10 carbon atoms, a halogen atom, a hydroxyl group or a mercapto group; k represents an integer of 0 to 3; when k is 2 or 3, Q may be same or different in a same ring; and X is a structure represented by the formula (2):

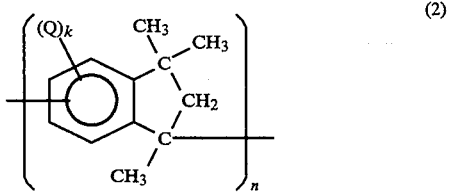

wherein Q and k are as defined above, and n is an average recurring unit number which is 0.5 to 20.